United States Patent [19]

Pallos

[11] 4,112,116
[45] Sep. 5, 1978

[54] CERTAIN CYCLOPROPANE THIOLCARBOXYLATES AND USE THEREOF AS MITICIDES

[75] Inventor: Ferenc M. Pallos, Walnut Creek, CA

[73] Assignee: Stauffer Chemical Company, Westport, Conn.

[21] Appl. No.: 742,803

[22] Filed: Nov. 18, 1976

[51] Int. Cl.$^2$ .................. A01N 9/12; C07C 153/09
[52] U.S. Cl. ........................ 424/301; 260/455 R
[58] Field of Search ................ 260/455 R; 424/301

[56] References Cited

U.S. PATENT DOCUMENTS

| | | | |
|---|---|---|---|
| 2,259,869 | 10/1941 | Allen | 260/455 R |
| 3,673,237 | 6/1972 | Janiak | 71/100 |
| 3,849,466 | 11/1974 | Henrick et al. | 260/455 R |

FOREIGN PATENT DOCUMENTS 2,219,710  4/1971  Fed. Rep. of Germany.

*Primary Examiner*—Lewis Gotts
*Assistant Examiner*—Robert C. Whittenbaugh
*Attorney, Agent, or Firm*—M. Henry Heines; Edith A. Rice

[57] ABSTRACT

Cyclopropane thiolcarboxylates of the formula

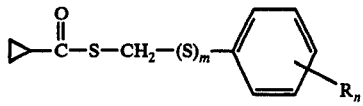

wherein R is halo or lower alkyl, $m$ is 0 or 1, and $n$ is 0, 1, 2, or 3 are effective miticides.

26 Claims, No Drawings

CERTAIN CYCLOPROPANE THIOLCARBOXYLATES AND USE THEREOF AS MITICIDES

This invention relates to novel benzyl and phenylthiomethyl cyclopropyl thiolcarboxylates that are miticidally active.

DISCUSSION OF THE PRIOR ART

German Offenlegungsschrift No. 2,219,710 to Shell International Research Maateschappij N.V. dated Nov. 9, 1972 discloses certain fungicidal 2,2-dihalo-cyclopropane carboxylate compounds. Included in the list of compounds is S-benzyl-2,2-dichloro-3,3-dimethylcyclopropanethiocarboxylate.

U.S. Pat. No. 3,849,466 to Clive A. Henrick et al., dated Nov. 19, 1975, discloses long chain aliphatic thiolesters of cyclopropionic acid compounds which are effective for the control of spider mites.

U.S. Pat. No. 2,259,869 to Clyve C. Allen teaches that compounds of the formula

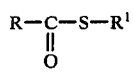

where R and R¹ are selected from various organic radicals, including benzyl and cyclopentyl are good fly repellents, and can also be used as a repellent against gnats, mosquitoes, etc.

U.S. Pat. No. 3,673,237 to Stefan Janiak discloses certain substituted phenyl cyclopropane thiolcarboxylates which are effective against the meal moth. The broader class of compounds disclosed in this patent are shown to be effective against spider mites and also effective as herbicides.

SUMMARY OF THE INVENTION

It has now been found that S-benzyl and phenylthiomethyl cyclopropane thiolcarboxylates having the general structural formula

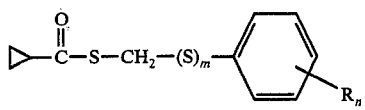

wherein R is selected from the group consisting of halogen and lower alkyl having 1-4 carbon atoms, $m$ is 0 or 1 and $n$ is 0, 1, 2, or 3 are highly effective against mites and exhibit little or no phytotoxicity.

The term "halogen" includes fluorine, chlorine, bromine and iodine. Chlorine is particularly preferred.

Lower alkyl radicals having 1–4 carbon atoms include methyl, ethyl, propyl, isopropyl, n-butyl, isobutyl, sec-butyl and tert-butyl.

Compounds of this invention can be prepared by reacting cyclopropane carboxylic acid chloride with the appropriate mercaptan in the presence of an acid acceptor. The reaction preferably takes place in an inert organic solvent such as benzene, toluene, methylene dichloride, glycol dimethyl ether and the like. The reaction temperature is not critical and temperatures from about 0° C to the boiling point of the solvent can be employed. For convenience, room temperature is preferred. Acid acceptors that can be used include tertiary amines, for example, triethylamine, pyridine, dimethylaniline and the like.

An alternate method of preparing the compounds of this invention is to react an alkali metal salt of cyclopropane thiolcarboxylate with the appropriate benzyl halide or phenylthiomethyl halide.

The following examples illustrate preparation of typical compounds of this invention and demonstrate their miticidal activity.

EXAMPLE 1

This example illustrates the preparation of 4-chlorobenzyl cyclopropane thiolcarboxylate.

A solution of 4.0 grams (0.025 mole) 4-chlorobenzylmercaptan and 2.6 grams (0.025 mole) cyclopropane carboxylic acid chloride in 25 milliliters benzene was prepared and stirred. Then 2.6 grams of triethylamine in 10 milliliters benzene was added dropwise to the reaction mixture. The reaction mixture was refluxed for two hours, cooled, then washed with water and dried over anhydrous magnesium sulfate. The product was then filtered and stripped of volatiles. A yield of 4.7 grams of a liquid product having a refractive index $N_D^{30}$ of 1.5549 was obtained. The structure of the product, 4-chlorobenzyl cyclopropane thiolcarboxylate, was confirmed by infrared and nuclear magnetic resonance spectroscopy.

EXAMPLE 2

This example illustrates the preparation of 4-chlorophenylthiomethyl cyclopropane thiolcarboxylate.

A solution of 2.1 grams of sodium hydrogen sulfide dissolved in 15 milliliters of ethanol was cooled in an ice water bath to about 4° C. Then 2.6 grams (0.025 mole) cyclopropane carboxylic acid chloride was added. The temperature rose to 36° C and the reaction mixture was cooled, with stirring, to 5° C. Then 4.8 grams (0.025 mole) 4-chlorophenyl thiomethyl chloride was added and the temperature was permitted to rise to room temperature. Ten grams (0.025 mole) of sodium hydroxide (2.0 grams 50% solution sodium hydroxide in water, further diluted with 10 milliliters of water) was added. The temperature rose to 50.5° C and the solution was permitted to cool to room temperature. About 15 milliliters of methylene dichloride were then added. The reaction mixture was washed three times with 10% aqueous solution of sodium bicarbonate and dried over anhydrous magnesium sulfate. The product was filtered and stripped of volatiles. A yield of 5.0 grams of a liquid product having a refractice index, $N_D^{30}$ of 1.5770. The structure of the product, 4-chlorophenylthiomethyl cyclopropane thiolcarboxylate, was confirmed by infrared and nuclear magnetic resonance spectroscopy.

Other compunds embodied by the present invention can be prepared in analogous manner using the appropriate starting materials, as will be readily apparent to one skilled in the art.

The following table lists illustrative compounds encompassed by this invention. Compound numbers have been assigned to them for convenience and are used throughout the balance of the specification.

TABLE I

| Compound No | | Refractive Index $N_D^{30}$ |
|---|---|---|
| 1 | S-4-chlorobenzyl cyclopropane thiolcarboxylate | 1.5549 |
| 2 | S-benzyl cyclopropane thiolcarboxylate | 1.4545 |

TABLE I-continued

| Compound No | | Refractive Index $N_D^{30}$ |
|---|---|---|
| 3 | S-3,4-dichlorobenzyl cyclopropane thiolcarboxylate | 1.5700 |
| 4 | S-4-methylbenzyl cyclopropane thiolcarboxylate | 1.5430 |
| 5 | S-2,4-dichlorobenzyl cyclopropane thiolcarboxylate | 1.5695 |
| 6 | S-2-chlorobenzyl cyclopropane thiolcarboxylate | 1.5600 |
| 7 | S-4-chlorophenylthiomethyl cyclopropane thiolcarboxylate | 1.5770 |

The compounds of this invention were tested for miticidal activity on Two-Spotted Mite [*Tetranychus urticae* (Koch)] using the following procedures:

Pinto bean plants (*Phaseolus sp.*) approximately 10 centimeters tall, are transplanted into sandy loam soil in three inch clay pots and thoroughly infested with two-spotted mites of mixed ages and sexes. Twenty-four hours later the infested plants are inverted and dipped for 2-3 seconds in 50—50 acetonewater solutions of the test compound. Treated plants are held in the greenhouse for seven days. Mortality is then determined for both the adult mites and the nymphs hatching from eggs which were on the plants at the time of treatment. Test concentrations range from 0.05% down to that at which 50% mortality occurs.

TABLE II

| Compound No. | Concentration for 50% Mortality | |
|---|---|---|
| | Adult Mites | Eggs |
| 1 | >.05 | .005 |
| 2 | >.05 | .01 |
| 3 | .03 | .005 |
| 4 | >.05 | .03 |
| 5 | .05 | .01 |
| 6 | >.05 | .01 |
| 7 | .04 | .003 |

> = greater than

As can be seen by the above data, the compounds of this invention can be used for affectively controlling mites. The compounds are particularly effective as a mite ovicide preventing the hatching of mite eggs.

The phytoxicity of representative compounds of this invention was tested and compared to the phytotoxicity of the corresponding phenyl compounds. The compounds tested were S-3,4-dichlorobenzyl cyclopropane thiolcarboxylate and S-3,4-dichlorophenyl cyclopropane thiolcarboxylate, S-2-chlorobenzyl cyclopropane thiolcarboxylate and S-2-chlorophenyl cyclopropane thiolcarboxylate. These tests use the standard tests used to demonstrate herbicidal activity of a chemical. These tests are as follows:

Pre-emergence herbicide screening test

Using an analytical balance, 20 mg of the compound to be tests is weighed out on a piece of glassine weighing paper. The paper and compound are placed in a 30 ml widemouth bottle and 3 ml of acetone containing 1% Tween 20R, a polyoxyethylene derivative of sorbitan monolaurate, is added to dissolve the compound. If the material is not soluble in acetone, another solvent such as water, alcohol or dimethylformamide (DMF) is used instead. When DMF is used, only 0.5 ml or less is used to dissolve the compound and then another solvent is used to make the volume up to 3 ml. The 3 ml of solution is sprayed uniformly on the soil contained in a small Styrofoam flat one day after planting weed seeds in the flat of soil. A No. 152 DeVilbiss atomizer is used to apply the spray using compressed air at a pressure of 5 lb/sq. inch. The rate of application is 8 lb/acre and the spray volume is 143 gal/acre.

On the day preceding treatment, the Styrofoam flat which is 7 inches long, 5 inches wide and 2.75 inches deep, is filled to a depth of 2 inches with loamy sand soil. Seeds of seven different weed species are planted in individual rows using one species per row across the width of the flat. The seeds are covered with soil so that they are planted at a depth of 0.5 inch. The seeds used are hairy crabgrass (*Digitaria sanguinalis*), watergrass (*Echinochloa crusgalli*), redroot pigweed (*Amaranthus retroflexus*), Indian mustard (*Brassica juncea*), curly dock (*Rumex crispus*), and Pinto beans (*Phaseolus vulgaris*), Ample seeds are planted to give about 20 to 50 seedlings per row after emergence depending on the size of the plants.

After treatment, the flats are placed in the greenhouse at a temperature of 70° to 85° F and watered by sprinkling. Two weeks after treatment the degree of injury or control is determined by comparison with untreated check plants of the same age. The injury rate from 0 to 100% is recorded for each species as percent control with 0% representing no injury and 100% representing complete kill.

Post-emergence herbicide screening test

Seeds of six plant species, including hairy crabgrass, watergrass, pigweed, mustard, curly dock and pinto beans (*Phaseolus vulgaris*) are planted in the Styrofoam flats as described above for pre-emergence screening. The flats are placed in the greenhouse at 70° to 85° F, and watered daily with a sprinkler. About 10 to 14 days after planting when the primary leaves of the bean plants are almost fully expanded and the first trifoliate leaves are just starting to form, the plants are sprayed. The spray is prepared by weighing out 20 mg of the test compound, dissolving it in 5 ml of acetone containing 1% Tween 20° and then adding 5 ml of water. The solution is sprayed on the foliager using a No. 152 DeVilbiss atomizer at an air pressure of 5 lb/sq. inch. The spray concentration is 0.2% and the rate is 8 lb/acre. The spray volume is 476 gal/acre.

Injury ratings are recorded 14 days after treatment. The rating system is the same as described above for the pre-emergence test.

The results of these tests are shown in Table III.

TABLE III

| | % CONTROL AT 8 LB/A. | | | | | | | | | | | |
|---|---|---|---|---|---|---|---|---|---|---|---|---|
| | Pre-Emergence | | | | | | Post-Emergence | | | | | |
| Compound | Crab-grass | Water-grass | Pig Weed | Curyl Dock | Mus-tard | Bean | Crab-grass | Water-grass | Pig Weed | Curly Dock | Mus-tard | Bean |
| S-3,4-dichlorobenzyl cyclopropane thiol-carboxylate | 0 | 0 | 0 | 0 | 0 | 0 | 20 | 40 | 0 | 0 | 0 | 0 |
| S-3,4-dichlorophenyl cyclopropane thiol-carboxylate | 0 | 0 | 95 | 0 | 0 | 0 | 98 | 40 | 0 | 100 | 100 | 30 |
| S-2-chlorobenzyl | | | | | | | | | | | | |

TABLE III-continued

| | % CONTROL AT 8 LB/A. | | | | | | | | | | | |
|---|---|---|---|---|---|---|---|---|---|---|---|---|
| | Pre-Emergence | | | | | | Post-Emergence | | | | | |
| Compound | Crab-grass | Water-grass | Pig Weed | Curyl Dock | Mus-tard | Bean | Crab-grass | Water-grass | Pig Weed | Curly Dock | Mus-tard | Bean |
| cyclopropane thiol-carboxylate | 0 | 0 | 0 | 0 | 0 | 0 | 90 | 10 | 0 | 30 | 0 | 0 |
| S-2-chlorophenyl cyclopropane thiol-carboxylate | 20 | 0 | 98 | 0 | 0 | 0 | 100 | 30 | 0 | 95 | 50 | 0 |

As can be seen by these results the S-benzyl cyclopropane thiolcarboxylates of this invention are considerably less phytotoxic than the corresponding S-phenyl compounds. The low phytotoxicity of the compounds of this invention make them particularly useful the control of mites on plant foliage.

The miticidal compounds of this invention are generally applied to the locus where control of mites is desired in the form of formulations containing the compound and an inert carrier. Miticidal formulations generally take the form of dusts, wettable powders, granules, solutions, emulsifiable concentrates, or the like.

Dusts are free-flowing powder compositions containing the miticidal compound impregnated on a particulate carrier. The particle size of the carrier is usually in the range of from about 30 to 50 microns. Examples of suitable carriers are talc, bentonite, diatomaceous earth, and pyrophyllite. Anticaking and antistatic agents can be added, if desired. The composition generally contains up to 50% of active ingredient.

Wettable powders are finely divided compositions comprising a particulate carrier impregnated with the miticidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols, salts of sulfonic acid, esters of long chain fatty acids and polyhydric alcohols and the like. A list of surface active agents suitable for use in agriculture formulations can be found in *Pesticide Formulations* by Wade Van Valkenburg, Marcel Dekker, Inc., N.Y. 1973 at pages 79-84.

Granules comprise the miticidal compound impregnated on a particulate inert carrier having a particle size of 1 to 2 millimeters in diameter. The granules can be made by spraying a solution of the active ingredient in a volatile solvent onto the granular carrier. Suitable carriers in preparation of granules include clay, vermiculite, sawdust, granular carbon, and the like.

The miticidal compounds can also be applied to the soil in the form of a solution in a suitable solvent. Solvents frequently used in pesticidal formulations include kerosene, fuel oil, xylene, petroleum fractions with boiling ranges above xylene, and aromatic petroleum fractions rich in methylated naphthalenes.

Emulsifiable concentrates consist of an oil solution of the miticide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate if desired.

The compositions are applied to the locus where control of mites is desired in a miticidally effective amount. In a preferred method of application, the miticide is applied as a solution or suspension from conventional spray apparatus. The solutions or suspensions contain about 0.01 to about 5.0%, preferably about 0.1 to about 2.0% by weight of the miticide.

What is claimed is:

1. A compound having the general structural formula

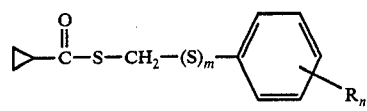

wherein R is selected from the group consisting of halogen and lower alkyl having 1-4 carbon atoms; m is 0 or 1; and n is 0, 1, 2, or 3.

2. The compound of claim 1 wherein m is 0.
3. The compound of claim 2 wherein $R_n$ is 4-chloro.
4. The compound of claim 2 wherein n is 0.
5. The compound of claim 2 wherein $R_n$ is 3,4-dichloro.
6. The compound of claim 2 wherein $R_n$ is 4-methyl.
7. The compound of claim 2 wherein $R_n$ is 2,4-dichloro.
8. The compound of claim 2 wherein $R_n$ is 2-chloro.
9. The compound of claim 1 wherein m is 1.
10. The compound of claim 9 wherein $R_n$ is 4-chloro.
11. A composition comprising a miticidally active compound having the general structural formula

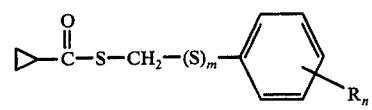

wherein R is selected from the group consisting of halogen and lower alkyl having 1-4 carbon atoms; m is 0 or 1; and n is 0, 1, 2 or 3; and an inert carrier therefor.

12. The composition of claim 11 wherein said miticidally active compound is S-4-chlorobenzyl cyclopropane thiolcarboxylate.
13. The composition of claim 11 wherein said miticidally active compound is S-benzyl cyclopropane thiolcarboxylate.
14. The composition of claim 11 wherein said miticidally active compound is S-3,4-dichlorobenzyl cyclopropane thiolcarboxylate.
15. The composition of claim 11 wherein said miticidally active compound is S-4-methylbenzyl cyclopropane thiolcarboxylate.
16. The composition of claim 11 wherein said miticidally active compound is S-2,4-dichlorobenzyl cyclopropane thiolcarboxylate.
17. The composition of claim 11 wherein said miticidally active compound is S-2-chlorobenzyl cyclopropane thiolcarboxylate.

18. The composition of claim 11 wherein said miticidally active compound is S-4-chlorophenylthiomethyl cyclopropane thiolcarboxylate.

19. A method for controlling mites which comprises applying to the locus where control is desired a miticidally effective amount of a compound having the general structural formula

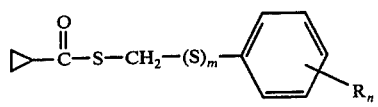

wherein R is selected from the group consisting of halogen and lower alkyl having 1-4 carbon atoms; $m$ is 0 or 1; and $n$ is 0, 1, 2, or 3.

20. The method of claim 19 wherein said compound is S-4-chlorobenzyl cyclopropane thiolcarboxylate.

21. The method of claim 19 wherein said compound is S-benzyl cyclopropane thiolcarboxylate.

22. The method of claim 19 wherein said compound is S-3,4-dichlorobenzyl cyclopropane thiolcarboxylate.

23. The method of claim 19 wherein said compound is S-4-methylbenzyl cyclopropane thiolcarboxylate.

24. The method of claim 19 wherein said compound is S-2,4-dichlorobenzyl cyclopropane thiolcarboxylate.

25. The method of claim 19 wherein said compound is S-2-chlorobenzyl cyclopropane thiolcarboxylate.

26. The method of claim 19 wherein said compound is S-4-chlorophenylthiomethyl cyclopropane thiolcarboxylate.

* * * * *